(12) United States Patent
Levy et al.

(10) Patent No.: US 9,084,877 B2
(45) Date of Patent: Jul. 21, 2015

(54) MAGNETIC TARGETING DEVICE, SYSTEM AND METHOD

(75) Inventors: Robert J. Levy, Merion Station, PA (US); Michael Chorny, Huntingdon Valley, IL (US); Ilia Fishbein, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 17 days.

(21) Appl. No.: 13/883,054

(22) PCT Filed: Oct. 27, 2011

(86) PCT No.: PCT/US2011/058029
§ 371 (c)(1),
(2), (4) Date: Jun. 27, 2013

(87) PCT Pub. No.: WO2012/061193
PCT Pub. Date: May 10, 2012

(65) Prior Publication Data
US 2013/0267762 A1    Oct. 10, 2013

Related U.S. Application Data

(60) Provisional application No. 61/481,447, filed on May 2, 2011, provisional application No. 61/410,156, filed on Nov. 4, 2010.

(51) Int. Cl.
*A61N 2/00*     (2006.01)
*A61K 9/50*     (2006.01)
(Continued)

(52) U.S. Cl.
CPC ............... *A61N 2/00* (2013.01); *A61K 9/5094* (2013.01); *A61K 9/5115* (2013.01); *A61L 29/14* (2013.01); *A61M 25/10* (2013.01)

(58) Field of Classification Search
CPC .................................. A61N 2/00; A61M 25/10
USPC ................................. 600/9–15; 128/897–899
See application file for complete search history.

(56) References Cited

U.S. PATENT DOCUMENTS

| 5,817,017 A | 10/1998 | Young et al. |
| 7,527,622 B2 | 5/2009 | Lane et al. |

(Continued)

FOREIGN PATENT DOCUMENTS

| WO | WO 01/35839 A2 | 5/2001 |
| WO | WO 2012/061193 A2 | 5/2012 |

OTHER PUBLICATIONS

International Search Report for International Application No. PCT/US2014/020122 dated Jun. 10, 2014.
(Continued)

*Primary Examiner* — John Lacyk
(74) *Attorney, Agent, or Firm* — RatnerPrestia

(57) ABSTRACT

A treatment system includes a magnetic targeting catheter and a plurality of MNP. The MNP may include one or more magnetic field-responsive agents and one or more therapeutic agents. The catheter may include an inner shaft having at least one lumen and a fluid delivery balloon adapted to administer a fluid from the inner shaft into a space surrounding the catheter. An expandable mesh formed of a magnetizable material may surround the fluid delivery balloon. The catheter may further include one or more occlusion balloons for controlling blood flow through a vessel in which the catheter is placed. A method of treating a medical condition may include advancing a magnetic targeting catheter to a site, deploying an expandable mesh connected to the catheter, applying a magnetic field to the mesh and depositing a plurality of MNP or cells loaded with MNP near the mesh.

46 Claims, 14 Drawing Sheets

(51) Int. Cl.
*A61K 9/51* (2006.01)
*A61L 29/14* (2006.01)
*A61M 25/10* (2013.01)

(56) References Cited

U.S. PATENT DOCUMENTS

| | | |
|---|---|---|
| 7,846,201 B2 | 12/2010 | Chorny et al. |
| 8,562,505 B2 * | 10/2013 | Levy et al. .................. 600/12 |
| 2002/0133115 A1 * | 9/2002 | Gordon et al. ............ 604/96.01 |
| 2002/0133225 A1 * | 9/2002 | Gordon ...................... 623/1.42 |
| 2006/0041182 A1 * | 2/2006 | Forbes et al. ................. 600/12 |
| 2006/0161103 A1 | 7/2006 | Constantz et al. |
| 2008/0006281 A1 * | 1/2008 | Sih et al. ..................... 128/899 |
| 2009/0082611 A1 | 3/2009 | Levy et al. |
| 2009/0216320 A1 | 8/2009 | Levy et al. |
| 2010/0204674 A1 | 8/2010 | Forbes et al. |
| 2010/0260780 A1 | 10/2010 | Levy et al. |

OTHER PUBLICATIONS

International Search Report for PCT/US 11/58029 dated May 25, 2012.

Notification Concerning Transmittal of International Preliminary Report on Patentability and Written Opinion, issued in related PCT Application No. PCT/US2011/058029, mailed May 16, 2013.

Colombian Office Action dated Jun. 26, 2014 in corresponding Colombian Application No. 13-122443, including English language translation.

Australian Office Action for Application No. 2011323685 Dec. 10, 2014.

Chinese Office Action for Application No. 201180053129.3 dated Sep. 4, 2014 (with English translation).

Office Action for Chinese Patent Application No. 201180053129.3 issued May 6, 2015.

* cited by examiner

MAGNETIC TARGETING DEVICE, SYSTEM AND METHOD

RELATED APPLICATIONS

This application is the U.S. National Phase Application under 35 U.S.C. §371 of PCT International Application No. US2011/058029 filed Oct. 27, 2011, which claims the benefit of priority of U.S. Application Ser. No. 61/410,156, filed Nov. 4, 2010, and claims the benefit of priority of U.S. Application Ser. No. 61/481,447, filed May 2, 2011, the contents of both applications being incorporated by reference in their entirety.

FIELD

This invention relates generally to therapeutic treatment of humans and animals, and more specifically to a system and method for delivering therapeutic compounds using a magnetic targeting device that is readily insertable into and removable from the human or animal.

BACKGROUND

The inventors have previously developed procedures for magnetic targeting of iron oxide-containing, magnetically responsive, biodegradable nanoparticles containing therapeutic agents to permanently deployed superparamagnetic stents in vivo. The feasibility of this approach has been demonstrated for delivering drugs, gene vectors and cell therapy. The inventors have also shown that targeting of MNP to permanent stents can be enhanced by application of a relatively uniform magnetic field. The following patents and published patent applications, which describe various aspects of magnetic targeting procedures, are incorporated herein by reference: U.S. Pat. No. 7,846,201, U.S. Pub. No. 2009/0216320, U.S. Pub. No. 2009/0082611, U.S. Pub. No. 2010/0260780, and International Pub. No. WO 2004/093643.

Targeted delivery of magnetic nanoparticles (MNP) has been performed by applying a uniform magnetic field to a permanent stent composed of a superparamagnetic material. Permanent stents have been used as targets based on the assumption that permanent implants ensure long term retention of MNP at the target site. Unfortunately, this approach is not an option for sites that do not have a permanent implant in place, but require treatment.

SUMMARY

Figure 1:
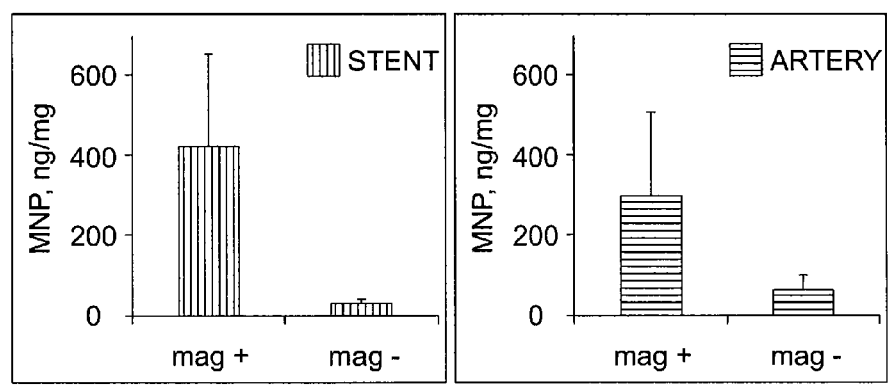
FIG. 1 shows levels of magnetic nanoparticle retention on a superparamagnetic stent and on an arterial wall (rat carotid) in the presence and in the absence of a uniform magnetic field (0.1 T) that was applied for 5 minutes.

A system for treating a medical condition in accordance with one embodiment of the invention includes a magnetic targeting catheter comprising a superparamagnetic material, and a plurality of MNP. The MNP may include one or more magnetic field-responsive agents and one or more therapeutic agents.

A device for treating a medical condition in accordance with the invention may include a catheter comprising a hollow tubular body and a delivery assembly attached to a distal end of the catheter. The delivery assembly may include an inflation tube extending through the catheter, the inflation tube having a distal end. An inner balloon may be attached to the distal end of the inflation tube. An injection tube may extend through the catheter, the injection tube having a distal end. An outer balloon may be attached to the distal end of the injection tube and enclose the inner balloon. The outer balloon may include a wall that is perforated by a plurality of pores extending through the wall. A control rod may extend through the catheter, the control rod having a distal end. A mesh may be attached to the distal end of the control rod and surround at least a portion of the outer balloon.

A method of treating a medical condition with one or more therapeutic agents in accordance with the invention may include the steps of advancing a magnetic targeting catheter to a site in a human or animal in need of the one or more therapeutic agents, and deploying an expandable mesh connected at the distal end of the magnetic targeting catheter, the mesh comprising a superparamagnetic material. The method may also include the steps of applying a uniform magnetic field to the mesh, using a dipole or more complex array of magnets to create this field, sufficient to temporarily magnetize the mesh, and, while applying the magnetic field, depositing near the mesh a plurality of MNP comprising one or more magnetic field-responsive agents and the one or more therapeutic agents. Magnetic mediated delivery may occur through several steps. During the application of the uniform field, the MNP are attracted to the mesh framework of the tip of the targeting catheter, that is in direct contact with the endothelial lining of the arterial wall. Other MNP locally delivered that are not bound to the mesh of the targeting catheter tip are scattered into the arterial wall, through the spaces in the meshwork of the device. This occurs due to the high force magnetic gradients created in the meshwork of the targeting catheter tip by the uniform magnetic field. When the uniform field is discontinued, MNP adherent to the device are no longer attracted to the superparamagnetic mesh, and are released from the mesh, and thus are taken up by the nearby arterial wall tissue (extracellular matrix and cells). The MNP may have ligands on a surface thereof capable of enhancing adhesion to tissue at the site. The method may further include the steps of undeploying the mesh and moving the magnetic targeting catheter to another location in the human or animal.

Another method of treating a medical with one or more therapeutic agents in accordance with the invention may include the steps of advancing a magnetic targeting catheter to a site in a human or animal in need of the one or more therapeutic agents, and deploying an expandable mesh connected at the distal end of the magnetic targeting catheter, the mesh comprising a superparamagnetic material. The method may also include the steps of applying a magnetic field to the mesh sufficient to temporarily magnetize the mesh, and, while applying the magnetic field, depositing near the mesh a plurality of cells loaded with MNP comprising one or more magnetic field-responsive agents and the one or more therapeutic agents. The method may further include the steps of undeploying the mesh and moving the magnetic targeting catheter to another location in the human or animal.

A device for delivering a fluid into a vessel may include an inner shaft comprising a proximal end, a distal end, and a hollow body extending between the proximal end and distal end. The hollow body may include at least one lumen extending through the inner shaft from the proximal end to the distal end. A fluid delivery balloon adapted to administer a fluid from the inner shaft into a vessel may surround the catheter. The fluid delivery balloon may include a balloon wall surrounding an interior space, the balloon wall forming at least one opening that extends through the balloon wall. The balloon wall may be disposed around a distal portion of the inner shaft, with the distal portion of the inner shaft comprising at least one port in fluid communication with the interior space of the fluid delivery balloon. An expandable mesh may surround the fluid delivery balloon. The expandable mesh may include a proximal end and a distal end, and may be formed of a magnetizable material.

DETAILED DESCRIPTION

The inventor has recently found that the permanent presence of a stent or other implant is not necessary to establish retention of MNP at a treatment location. Rather, the inventor has found that a removable or "temporary" magnetic targeting device, such as a magnetic targeting catheter, can be used to target MNP to a specific site, where the MNP will be retained. The inventor has found that there are many advantages to using a magnetic targeting catheter as opposed to a permanent implant. A magnetic targeting catheter may be used to magnetically deliver MNP in virtually any setting, such as an artery or other tissue location, including areas containing permanent implants (e.g., nonmagnetic metals such as nitinol, biodegradable stents etc. can also be targeted). A magnetic targeting catheter can also be used in sites where no implant has been deployed, such as arteries only treated with balloon angioplasty—a procedure still used for some cases of peripheral arterial disease (PAD). Unlike a permanent implant, a magnetic targeting catheter can be moved to different locations within a diseased artery or other location, allowing treatment to be applied with the same temporary device at different locations before removing the magnetic targeting catheter. Because magnetic targeting and arterial wall uptake occur rapidly, multiple regions of a diseased artery can be treated using a magnetic targeting catheter, which may be employed in a catheterization procedure.

Accordingly, one aspect of the invention provides a system and method for delivery of MNP containing a therapeutic agent to a temporary magnetic targeting device in a diseased artery or other location. With the temporary device, system and method, MNP can be targeted to and deposited at a site without leaving a stent or other implant behind.

The devices, systems and methods of the invention can be used for delivering MNP comprising a therapeutic agent to catheter-accessible sites in a human or animal subject. Various medical conditions may be treated in this manner. For example, various pathologic conditions may be treated, such as arterial disease and other disorders presently treated by stent intervention, including urologic diseases, conditions requiring bronchial stents, and gastrointestinal conditions treated by stent deployment, such as the use of bile duct stents. For simplicity, the inventors will concentrate their description of the invention on treatment of arterial disease, but it will be understood that in its broadest form the invention is applicable to treatment of many different sites in a human or animal subject.

The devices, systems and methods of the invention may feature a magnetic targeting device having a design suited for temporary placement in an artery or other site in need of treatment, and comprising a superparamagnetic material. In a preferred embodiment, the magnetic targeting catheter includes a catheter and expandable wire mesh, the mesh being integral with or permanently affixed to the catheter. The devices, systems and methods of the invention may also feature a plurality of MNP. In preferred embodiments, the MNP have surface modifications to increase arterial wall adhesion (or adhesion to tissue at any other relevant targeted site, such as a bile duct etc. as described above). As an alternative to MNP, the device, system and method of the invention may instead deliver cells loaded with MNP.

Devices, systems and methods of the invention may further include a magnetic filter that can be used at a location "downstream" of the magnetic targeting catheter to trap and remove nontargeted MNP. As used herein, the term "nontargeted" refers to magnetic nanoparticles that have escaped capture by the magnetic targeting catheter and arterial wall. The filter may be a component that is completely separate from the magnetic targeting catheter, or a component of the magnetic targeting catheter, as will become apparent in the examples that follow.

Furthermore, devices, systems and methods of the invention may include one or more occlusion balloons designed to temporarily occlude an artery and limit flow in the artery while the MNP are targeted to the arterial wall. Limiting flow in the artery can reduce "washout", which occurs when arterial flow pulls MNP or cells from the arterial wall after the MNP or cells reach the arterial wall. Reducing washout enhances MNP and cell retention in the targeted arterial segment. Like the filter, the occlusion balloons may be completely separate from the magnetic targeting catheter, or a component of the magnetic targeting catheter.

Excellent targeting and retention is possible using a magnetic targeting catheter containing superparamagnetic material (e.g., 304, 420, 430 stainless steel, and others). In addition to using superparamagnetic material, excellent targeting and retention is possible with MNP having enhanced arterial wall adhesion due to affinity-surface modification of the targeted MNP. The magnetic targeting catheter may be constructed from a custom made catheter. The catheter may be used to access a location within a diseased artery. The location may have been previously stented by a non-magnetically responsive stent, or may still contain a stent. Once the magnetic targeting catheter is passed through the artery to the treatment site, a uniform magnetic field is applied in the area of the magnetic targeting catheter, for a period of time sufficient to provide good capture of MNP at the site. A period of 5 minutes (or other durations, depending on conditions) may be sufficient to establish MNP retention. This is demonstrated in FIG. 1, which shows levels of magnetic nanoparticle retention on a superparamagnetic stent and on an arterial wall (rat carotid) in the presence and in the absence of a uniform magnetic field (0.1 T) that was applied for 5 minutes. At the conclusion of the 5 minute magnetic field exposure, the animal was immediately euthanized and the stent removed for separate analyses for magnetic nanoparticle levels compared to the stented arterial wall segment. The end of this description summarizes the study that was performed, and describes the testing procedure and data that was collected.

It should be noted that permanently implanted stents are required in most cases of PAD to both acutely relieve obstruction and to "scaffold", that is, give proper mechanical support to, the artery to promote healing at vulnerable plaque regions. Therefore, one embodiment of the invention involves placement of a permanent stent for PAD in a primary procedure, and once stable deployment is achieved, carrying out a vascular magnetic intervention with a magnetic targeting catheter for magnetic targeting purposes only. Similarly, if an artery has previously been subjected to a stent procedure with a permanent stent in place, a suitable series of procedures may involve: 1) diagnosing the site of obstruction; 2) carrying out a procedure to mechanically relieve the obstruction, such as balloon dilation or using a rotating-blade atherectomy catheter; and 3) carrying out a vascular magnetic intervention using a magnetic targeting device to deliver MNP with a therapeutic cargo to the arterial wall.

Each of the components of the device, system and method will now be described in detail.

Magnetic Targeting Devices

Commonly used permanent stents do not employ superparamagnetic materials and are therefore incapable of being temporarily magnetized to a significant level by an externally applied magnetic field. Thus, they cannot strongly attract magnetic nanoparticles. In contrast, magnetic targeting devices in accordance with the invention, such as magnetic targeting catheters, are made of superparamagnetic materials such as stainless steel, HyMu 80® alloy, and other materials, which are suitable for use according to the invention. Such magnetic targeting catheters can be deployed in an arterial region, with or without a stent already in place, and then exposed to a uniform magnetic field to temporarily magnetize the magnetic targeting device and enable the device to be targeted with MNP. The following are several examples of magnetic targeting devices in accordance with different exemplary embodiments of the invention.

Example 1

Figure 2A:
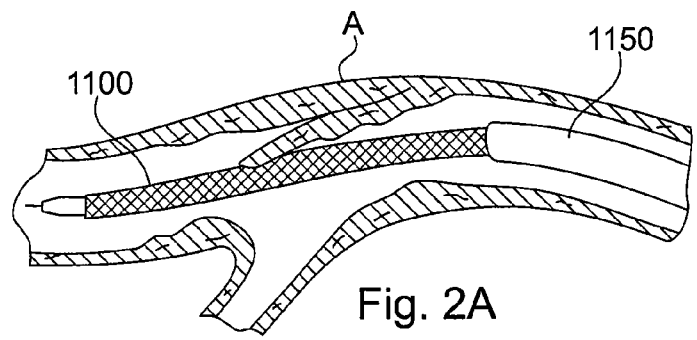
FIGS. 2A, 2B and 2C show placement, deployment, and withdrawal respectively of a magnetic targeting device during treatment with MNP according to the invention.
Figure 2B:
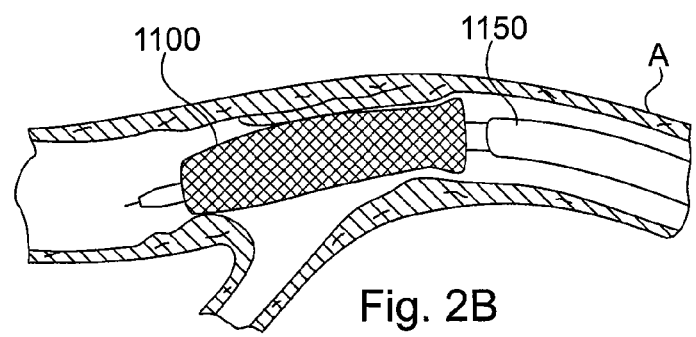
Figure 2C:
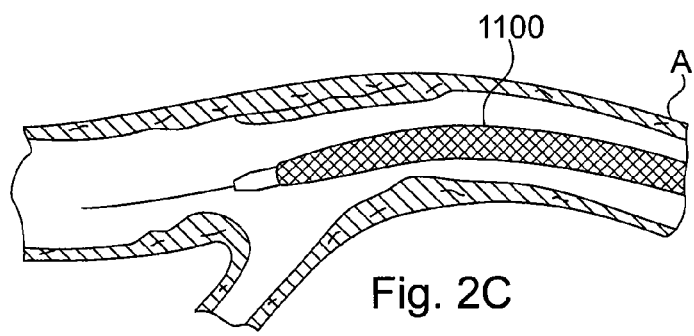

In a first example shown in FIGS. 2A-2C, a temporary arterial stent 1100 mounted on a catheter 1150 is used as a magnetic targeting device in accordance with the invention. The stent 1100 is made from a superparamagnetic steel (stainless steel), permanently positioned on the tip of the catheter 1150. Stent 110 and catheter 1150 are advanced inside an artery A to an obstructed area as shown in FIG. 2A. Stent 1100 is then deployed while still attached to the catheter 1150, as shown in FIG. 2B. A uniform magnetic field (typically about 0.1 T) is then created over the region of the artery using techniques described in Proc. Natl. Acad. Sci. U.S.A. 2010 May 4; 107(18):8346-51, incorporated herein by reference. Upon creating the field, therapeutic MNP are deposited near stent 1100. After a short time, for example 1 to 5 minutes, the field is discontinued. Stent 1100 is undeployed and the catheter and stent are withdrawn, as shown in FIG. 2C.

Example 2

Figure 3A:
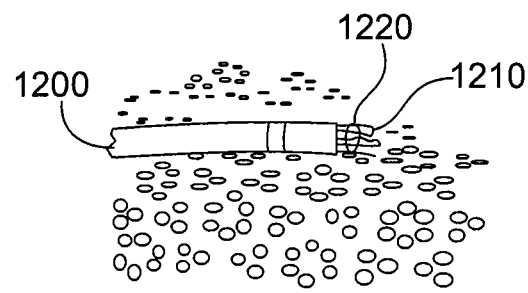
FIGS. 3A and 3B show retracted and deployed views of an alternative device suitable for use as a magnetic targeting device according to the invention.
Figure 3B:
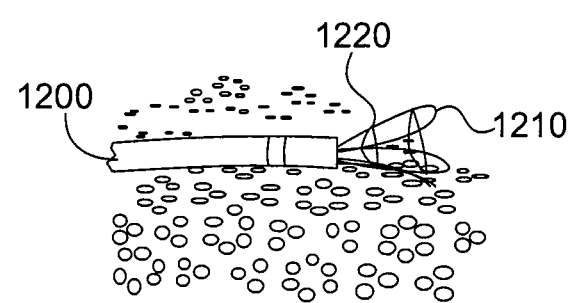

FIGS. 3A and 3B show another device 1200 suitable for use as a magnetic targeting device according to the invention. Device 1200 would more typically be referred to as a catheter-delivered retractable snare, but it may be used as an embodiment of a magnetic targeting device for purposes of this invention. Device 1200 may be made by modifying a commercially available nitinol-loop snare catheter, such as a catheter sold under the trademark EN Snare® by Merit Medical, Inc. The catheter has three self expanding loops 1210 of nitinol coming out of the end of the catheter, and is typically used for snaring intravascular devices such as inferior vena cava (IVC) filters. Loops 1210 are surrounded by 304 stainless steel wires 1220, which are spirally wrapped around each of the loops. The steel wires 1220 positioned on the outside of the loops 1210 provide arterial contact when deployed and can be withdrawn with retraction. Such a device can perform much the same function as the temporary 304 stainless steel stent described above, i.e., magnetization during uniform field exposure to enable MNP targeting to the regional arterial wall. Other temporary stents suitable for use according to the invention are disclosed in U.S. Pat. No. 4,456,667 to Ham et al., the entirety of which is incorporated herein by reference.

Example 3

Figure 4:
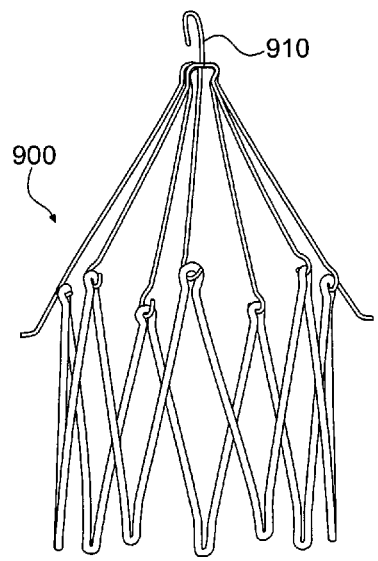
FIG. 4 shows an exemplary IVC filter that may be used as a magnetic targeting device according to the invention.

Temporary targeting devices for arterial use according to the invention need not be affixed to the end of a catheter. For example, IVC filters used to block the migration of thromboemboli from the lower extremities to the lungs (where they might cause fatal pulmonary emboli), may also be used as targeting devices according to the invention. IVC filters may be designed to be deployed and left in place without an attached catheter. They are retrieved after the risk of pulmonary embolism is no longer present, using a custom designed snare catheter. An exemplary IVC filter 900 is shown in FIG. 4. Filter 900 includes a hook 910 that can be accessed with a snare-tipped catheter to allow retrieval of the device.

Example 4

Figure 5:
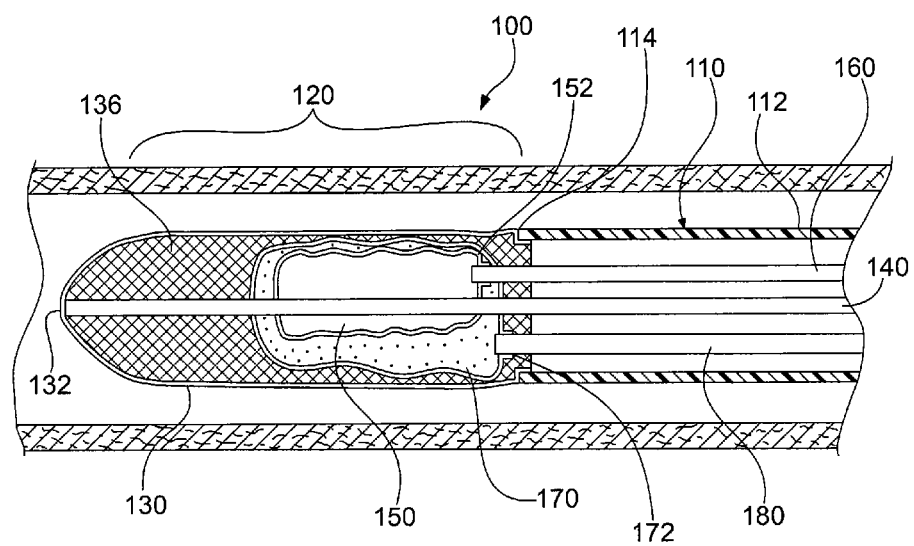
FIG. 5 is a truncated schematic view of another magnetic targeting device in accordance with the invention, shown in a first mode of operation inside a blood vessel.
Figure 6:
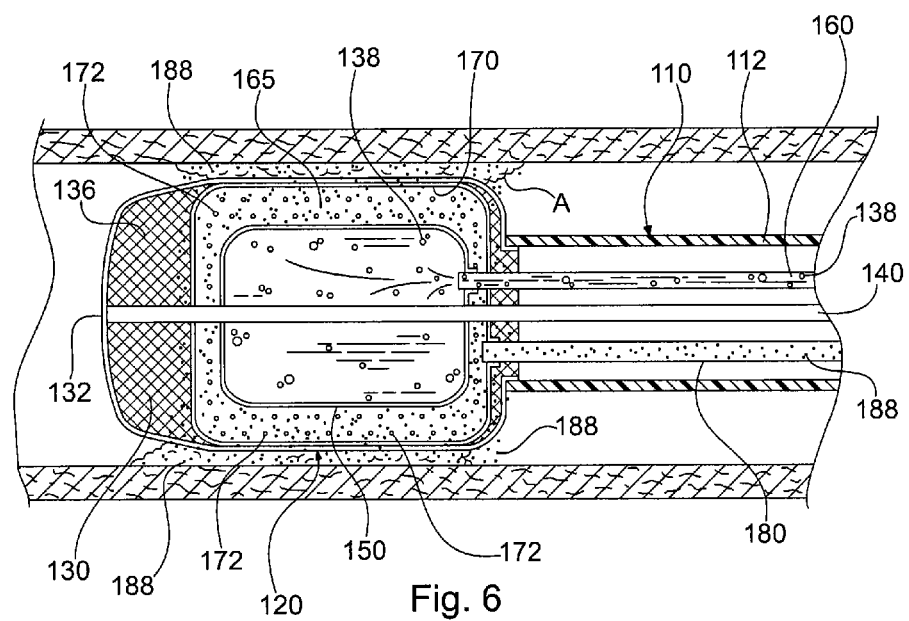
FIG. 6 is a truncated schematic view of the magnetic targeting device of FIG. 5, shown in a second mode of operation inside a blood vessel.

Referring to FIGS. 5 and 6, another magnetic targeting catheter 100 is schematically shown in accordance with the invention. Magnetic targeting catheter 100 is operable in a collapsed condition, as shown in FIG. 5, and an expanded condition, shown in FIG. 6. Magnetic targeting catheter 100 includes a catheter portion 110 and a delivery assembly 120. Catheter portion 110, which is truncated for clarity, has a hollow tubular body 112 with a distal end 114. Distal end 114 is attached to the delivery assembly 120. Delivery assembly 120 is operable from a remote location outside of the body to deliver MNP to a treatment site in an artery or other location.

Magnetic targeting catheter 100 can be used to direct MNP, or cells containing MNP, to an arterial wall under the application of a uniform magnetic field. For simplicity, the reference number 188 will be used as a reference for MNP, cells loaded with MNP, or suspensions containing either MNP or cells loaded with MNP.

Magnetic targeting catheter 100 includes a number of components that can be collapsed or retracted to a narrow profile for advancement through an artery, and subsequently expanded to contact or approach the arterial wall. In particular, delivery assembly 120 includes an expandable wire mesh 130 that is constructed much like an expandable stent. Mesh 130 is mounted to distal end 114 of catheter portion 110. A control rod 140 extends through the catheter portion 110 and connects with a distal end 132 of mesh 130.

Control rod 140 can be advanced distally relative to the catheter by a pushing action, which collapses the mesh. That is, control rod 140 can be pushed distally so the cross-sectional area of the mesh is reduced to a size substantially smaller than the cross-sectional area inside the artery, as illustrated in FIG. 5. In the collapsed state, magnetic targeting catheter 100 can be moved easily moved within the artery without contacting the arterial wall. Control rod 140 can also be pulled proximally relative to the catheter portion to expand the mesh. That is, control rod 140 can be pulled back (i.e. in a rearward direction) to enlarge the cross-sectional area of the mesh 130, as illustrated in FIG. 6. Mesh 130 can be expanded so that the periphery of the mesh is in contact with, or in close proximity to, a section of the arterial wall to be treated. FIG. 6 shows an area A having an arterial obstruction that is being targeted with magnetic targeting catheter 100.

Mesh 130 includes a plurality of mesh wires 136 that are formed of a flexible elastic material. The material preferably has an elasticity that allows the mesh to readily expand upon pulling control rod 140, and collapse to its original unexpanded shape upon pushing the control rod. Mesh 130 is also formed of a superparamagnetic material, such as stainless steel 304, 420 or 430. The spacings between wires 136 are specifically designed in accordance with the size of MNP or cells to be delivered. Where MNP are to be delivered, wires 136 preferably have spacings that range between about 5 MNP diameters to about 10 MNP diameters. Moreover, each wire 136 preferably has a diameter ranging between about 2 MNP diameters to about 10 MNP diameters. The diameters of MNP generally range in size from about 50 nm to about 500 nm.

Where cells are to be delivered, the mesh wires have spacings ranging between about 5 cell diameters to about 10 cell diameters. Each wire 136 preferably has a diameter ranging between about 2 cell diameters to about 10 cell diameters. The diameters of the cells range in size from between about 5 micrometers to about 15 micrometers.

Mesh 130 contains an inner balloon 150 and an outer balloon 170, the outer balloon extending between the inner balloon and the mesh as shown. Catheter portion 110 contains an inflation tube 160 that fluidly connects with a proximal end 152 of inner balloon 150. Catheter portion 110 also contains an injection tube 180 that fluidly connects with a proximal end 172 of outer balloon 170. Inner balloon 150 is inflatable and deflatable by introducing and removing a fluid 138, respectively, into and out of the inner balloon. Fluid 138 may be gas (e.g. $CO_2$) or a liquid (e.g. saline). As inner balloon 150 inflates, the cross-sectional area of the inner balloon expands until the outer periphery of the inner balloon contacts the wall of outer balloon 170. Outer balloon 170 is formed of a flexible material with a small wall thickness that allows it to expand in response to expansion of inner balloon 150 after the inner balloon contacts the outer balloon.

Outer balloon 170 surrounds inner balloon 150, as noted above, creating a plenum or space 165 between the balloons. The wall 171 of outer balloon 170 is perforated, forming a number of tiny openings or pores 172 that extend through the balloon wall. Each pore 172 provides a fluid passage between space 165 and the exterior of outer balloon 170. Pores 172 may be arranged uniformly around outer balloon 170. Each pore 172 dilates or expands as outer balloon 170 expands. Pores 172 are sized so as to be large enough to allow the release of MNP or cells 188 through outer balloon 170 when the pores are dilated. Injection tube 180 has a proximal end (not shown) that is connectable to a source of MNP or cells 188. In this arrangement, MNP or cells 188 can be injected from a remote location into the injection tube 180 and into the space between the inner balloon 150 and outer balloon 170.

Before inserting magnetic targeting catheter 100 into the body, the magnetic targeting catheter is brought to an undeployed state, as shown in FIG. 5. That is, the components of delivery device 120, including but not limited to mesh 130, inner balloon 150 and outer balloon 170, are collapsed. Specifically, mesh 130 is retracted, and inner and outer balloons 150 and 170 are deflated. This reduces the cross-sectional profile of magnetic targeting catheter 100, making it easier to insert and maneuver the magnetic targeting catheter through an artery. All components of delivery portion 120, including but not limited to mesh 130, inner balloon 150, inflation tube 160, outer balloon 170 and injection tube 180, can be operated and controlled from the proximal end of catheter portion 110.

Catheter portion 110 is advanced into the artery until delivery portion 120 is positioned at a desired location for treatment, for example, obstruction A in FIG. 6. Control rod 140 is then pulled back to expand the mesh 130. In particular, the control rod 140 is pulled rearwardly, or in the proximal direction relative to catheter portion 110, to expand mesh 130 so that mesh wires 136 contact the obstruction A and arterial wall. Inner balloon 150 is then inflated to expand the inner balloon and outer balloon 170, and bring the outer balloon in close proximity to the arterial wall just inside mesh 130. In the expanded state, pores 172 in outer balloon 170 are enlarged, opening up conduits that are sufficiently large to pass a MNP suspension or cell suspension through the outer balloon wall 171.

After outer balloon 170 is expanded, a uniform magnetic field is applied to the arterial area around mesh 130, creating magnetic gradients in the mesh wires 136. The uniform magnetic field (typically about 0.1 T) is created over the region of the artery, and may created using techniques described in Proc. Natl. Acad. Sci. U.S.A. 2010 May 4; 107(18):8346-51, incorporated herein by reference.

A MNP suspension or cell suspension 188 is then injected through injection tube 180 and into space 165 between the inner balloon 150 and outer balloon 170. The MNP or cell suspension 188 that enters space 165 discharges through pores 172 and exits the outer balloon 170. At this stage, the MNP or cells 188 are attracted to mesh wires 136 under the influence of the magnetic field. Some or all of the mesh wires 136 are in contact with the arterial wall. As such, the MNP or cells 188 are deposited on the arterial wall as they contact the wires. The magnetic field is applied over a sufficient time period to deposit MNP or cells on the arterial wall. The time period may vary depending on several variables. Under most conditions, the time period will range from about 1 minute to about 5 minutes. Sufficient MNP and cell retention may be achieved with shorter or longer time periods, however.

After the magnetic field is applied for a sufficient time, the magnetic field is removed, and inner balloon 150 is deflated to collapse the inner balloon and outer balloon 170. Mesh 130 is then retracted by pushing control rod 140 to expand the length of the mesh and reduce the cross-sectional profile of magnetic targeting catheter 100. Magnetic targeting catheter 100 can then be withdrawn from the artery, or advanced to another location in the artery where the treatment steps described above are repeated.

Example 5

Devices and systems in accordance with the invention may include a downstream arterial filter or trap. The filter may be used according to the invention to trap nontargeted MNP. The filter may include a superparamagnetic material, for example in the form of a mesh (e.g., 304, 420, or 430 stainless steel), and thereby become temporarily magnetized by the same field that temporarily magnetizes the stent. Some MNP remain adherent to the filter through protein-surface interactions after cessation of the field, as in the stent adhesion shown in FIG. 1. Alternatively, the filter may contain small permanent magnets to capture nontargeted MNP.

The filter may additionally be surface-modified with moieties promoting adhesion to the MNP. For example, the filter may be functionalized with one element of a biotin-avidin affinity pair while the other element of the pair is used as a ligand that is bound to the core of the nanoparticle. In one exemplary embodiment, the MNP may be surface-functionalized with biotin as follows. MNP are formulated as previously described (Proc. Natl. Acad. Sci. U.S.A. 2010 May 4; 107(18):8346-8351) with bovine serum albumin as a surface stabilizer, and then derivatized with biotin. In an exemplary procedure, 5 mg of sulfo-N-hydroxysuccinimidyl biotin are added to 1 ml of MNP suspension, and allowed to react for 1 hour at 4° C. The biotin-modified particles are then separated from unincorporated substances by two cycles of magnetic decantation.

If the filter includes a polymeric component (for example, a membrane) in addition to the magnetic or magnetizable component, avidin may be attached to the filter by using a benzophenone-containing polymer such as described in U.S. Pat. No. 7,635,734. Photoactivation of this polymer on the surface of the polymeric filter membrane creates a pyridyldithio-enriched surface, which may then be functionalized by reaction with a thiol-modified avidin. The latter may be produced by reaction of avidin with a bifunctional crosslinker such as N-succinimidyl 3-[2-pyridyldithio]-propionate (SPDP) or by converting lysine amino groups on the avidin to thiols using Traut's reagent.

If the filter does not include a polymeric component but only a metal such as stainless steel, the polybisphosphonate coordination chemistry described in U.S. Pat. No. 7,589,070, incorporated herein by reference, may be used for attaching Avidin to the metal. The downstream arterial filter in accordance with the invention may either be a separate standalone instrument, or a component of a magnetic targeting catheter.

FIGS. 7A-7D illustrate one possible embodiment of an arterial filter 2000 in accordance with the invention. Filter 2000 may be include a collapsible mesh having strands formed of super-paramagnetic steel, such as 304, 420, or 430 stainless steel. Alternatively, the strands may be formed of a drawn filled tubing having a composite structure, as described in Example 8 below. In use, filter 2000 forms a trap that can be magnetized in a uniform field. When magnetized, filter 2000 traps extraneous MNP that are not retained by the targeting device during magnetic targeting. This reduces the possibility of end-organ toxicity and systemic MNP exposure.

Figure 7A:
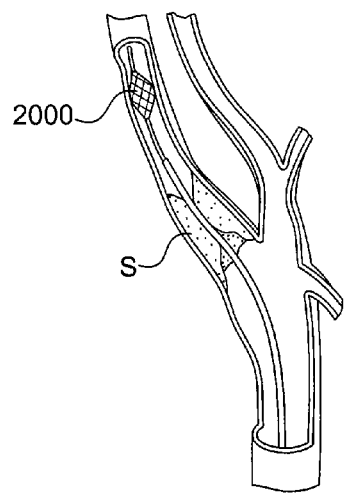
FIGS. 7A, 7B, 7C and 7D show various stages of using a magnetic or magnetizable arterial filter deployed downstream during carotid stenting, according to the invention.
Figure 7B:
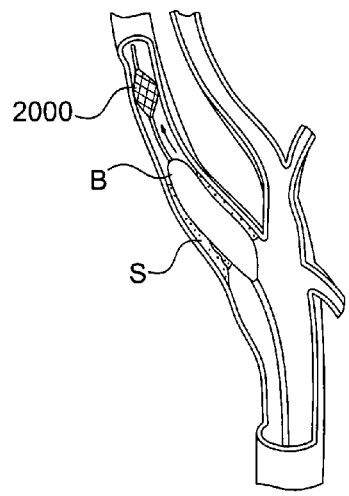
Figure 7C:
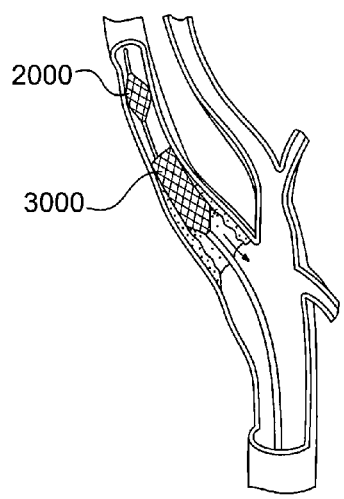
Figure 7D:
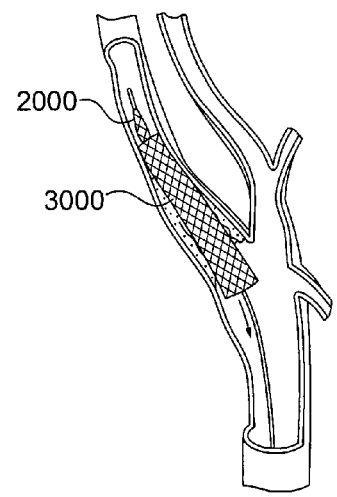

Filter traps in accordance with the invention can be used with various targeting devices in different procedures. In FIGS. 7A-7D, for example, filter 2000 is used in combination with a stent deployment and balloon catheterization. In a first step, filter 2000 is placed downstream of a treatment site S, as shown in FIG. 7A. After filter 2000 is properly positioned, a balloon angioplasty may be performed with a balloon catheter B, as shown in FIG. 7B. Balloon B is then retracted and a stent is deployed at treatment site S. FIG. 7C shows a stent 3000 in the process of being expanded at treatment site S. As with the filter 2000, stent 3000 may be formed of superparamagnetic steel, such as 304, 420, or 430 stainless steel, or a drawn filled tubing having a composite structure. A uniform magnetic field (0.1 T) is applied to the stent 3000, followed by injection of MNP. A plurality of MNP are captured by the temporarily magnetized stent, while filter 2000 traps particles escaping capture by the stent. After the uniform magnetic field is removed, the targeting and delivery system is removed. The filter 2000 may be collapsed, as shown in FIG. 7D and withdrawn through the stent 3000.

Example 6

Figure 8:
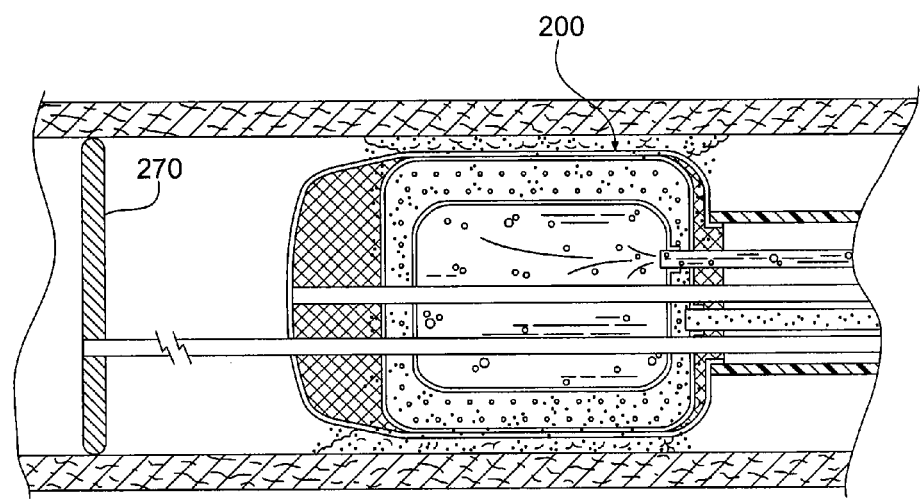
FIG. 8 is a truncated schematic view of a magnetic targeting device in accordance with another exemplary embodiment of the invention inside a blood vessel.

Referring to FIG. 8, a magnetic targeting catheter 200 is shown in accordance with another exemplary embodiment of the invention. Magnetic targeting catheter 200 includes all the same components that magnetic targeting catheter 100 includes, plus an expandable filter or trap 270. Trap 270 is designed for placement downstream of the treatment site to trap MNP or cells that do not adhere to the arterial wall or mesh. The trap 270 is formed of an elastic superparamagnetic material that may be the same material used for the mesh. Trap 270 is expandable and retractable with a second control rod 260, similar to the control rod used to deploy the mesh.

In use, trap 270 is expanded prior to applying the magnetic field. Once trap 270 is expanded and the field applied, the MNP or cells are injected. Nontargeted MNP or cells that are not retained by the mesh and arterial wall can be captured downstream in trap 270.

Example 7

The system further contemplates devices featuring one or more occlusion balloons intended to temporarily occlude the artery and limit flow in the artery while the MNP are targeted to the arterial wall. Limiting flow in the artery can reduce "washout", which occurs when arterial flow pulls MNP or cells from the arterial wall after the MNP or cells reach the arterial wall. This enhances MNP and cell retention in the targeted arterial segment.

Figure 9:
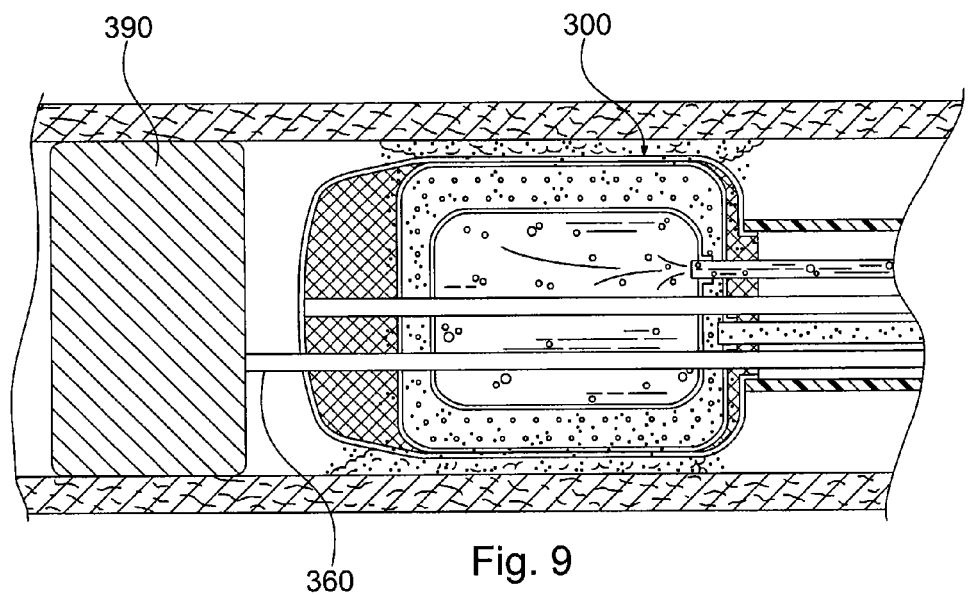
FIG. 9 is a truncated schematic view of a magnetic targeting device in accordance with another exemplary embodiment of the invention inside a blood vessel.

Referring to FIG. 9, a magnetic targeting catheter 300 is shown in accordance with another exemplary embodiment of the invention. Magnetic targeting catheter 300 includes all the same components that magnetic targeting catheter 100 includes, plus an occlusion balloon 390. Occlusion balloon 390 is inflatable with an inflation tube 380 that is shown as a separate tube from the inflation tube 360 that inflates inner balloon 370. The inflation tube connected to the occlusion tube may alternatively be an extension of the inflation tube connected to the inner balloon. In use, occlusion balloon 390 is inflated just prior to MNP or cell injection. After discontinuation of the magnetic field, the occlusion balloon is deflated to restore arterial flow.

Example 8

Referring now to FIGS. 10-13, a magnetic targeting catheter 600 with integrated occlusion balloons is shown in accordance with another exemplary embodiment of the invention. Magnetic targeting catheter 600 includes an inner shaft 610 comprising a proximal end 612, a distal end 614, and a hollow body 613 extending between the proximal end and distal end. Hollow body 613 contains a number of lumens extending through the inner shaft from the proximal end to the distal end, as will be described in more detail below. Magnetic targeting catheter 600 also includes a fluid delivery balloon 620 and an expandable mesh 630 surrounding the fluid delivery balloon. The fluid delivery balloon is adapted to administer a fluid from inner shaft 610 into a vessel surrounding the catheter. Fluid delivery balloon 620 includes a balloon wall 622 surrounding an interior space 621. The balloon wall 622 forms a number of small openings 624 that extend through the balloon wall. Openings 624 are adapted to allow a suspension of MNP to be targeted to the expandable mesh 630 when a uniform magnetic field is applied to the mesh. The balloon wall 622 is disposed around a distal portion of inner shaft 610, with the distal portion of the inner shaft having a first port 616 and a second port 618 in fluid communication with the interior space of the fluid delivery balloon. First port 616 is configured to fill fluid delivery balloon 620 with a MNP suspension, and second portion 618 is configured to flush or remove fluid from the fluid delivery balloon.

Expandable mesh 630 has a proximal end 632 and a distal end 634, and is formed of a magnetizable material. Mesh 634 may have strands 635 formed of 304 stainless steel wire. Alternatively, the strands 635 may have a composite structure formed in a drawn filled tubing process. Mesh 630, for example, may be formed in a drawn filled tube having an interior core formed of a nickel-iron-molybdenum alloy, such as HyMu 80® alloy manufactured by Carpenter Technology Corp., and an outer shell or sheath made of 35N LT alloy. HyMu 80® alloy is an unoriented, 80% nickel-iron-molybdenum alloy. Strands formed of HyMu 80® alloy have shown decreased residual magnetization after removal of the magnetic field from the mesh. Decreased residual magnetization limits the potential for MNP to be retained on the mesh, rather than the treatment site, after the magnetic field is removed, and after the mesh is retracted and removed from the treatment site: Ni alloy is sealed within the drawn filled tubing to essentially prevent Nickel exposure. The 35N LT alloy provides a mechanical spring function that makes the mesh strands more resilient.

Magnetic targeting catheter 600 includes a pair of integrated occlusion balloons adapted to inflate and constrict a section of a vessel surrounding the catheter. A first occlusion balloon 640 is located proximally with respect to expandable mesh 630, and a second occlusion balloon 650 is located distally with respect to the expandable mesh. First occlusion balloon 640 can be inflated with a gas or liquid to constrict the artery at a location upstream from the treatment site and temporarily stop the flow of blood to the treatment site. Similarly, second occlusion balloon 650 can be inflated to constrict the artery at a location downstream from the treatment site and temporarily stop the flow of blood from the treatment site. First and second occlusion balloons 640 and 650 are independently operable to control flow through the artery past the treatment site, and one may be inflated while the other is deflated, if the need for such operation arises. When first and second occlusion balloons 640 and 650 are both inflated to constrict the artery, flow to and from the treatment site is halted, creating a static condition. In the static condition, a suspension of MNP can be administered to the treatment site and targeted to the vessel wall under a uniform magnetic field. The static condition minimizes the potential for MNP being pulled into the bloodstream and carried away from the treatment site, as discussed earlier.

Figure 14:
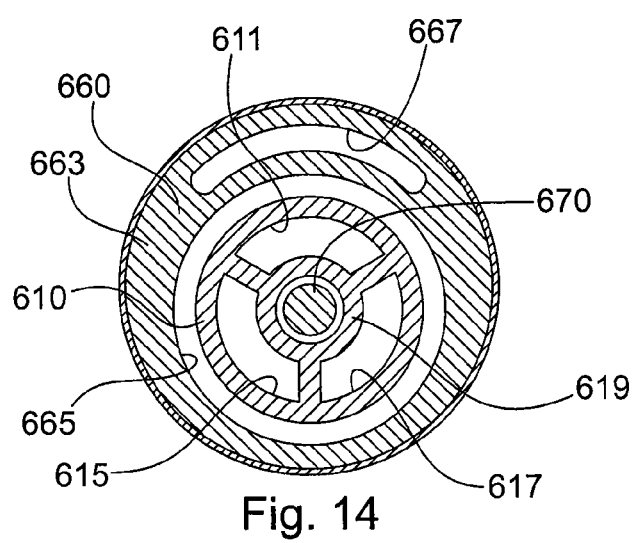
FIG. 14 is a cross sectional view of the magnetic targeting device in FIG. 10, taken through line 14-14 in FIG. 10.

Magnetic catheter device 600 further includes an outer shaft 660 extending over at least a portion of the inner shaft 610. Outer shaft 660 includes a proximal end 662, a distal end 664, and hollow body 663 extending between the proximal end and distal end. Referring to FIG. 14, hollow body 663 forms a primary lumen 665 and a secondary lumen 667, the primary and secondary lumens extending from the proximal end 662 of the outer shaft to the distal end 664. Primary lumen 665 is offset from the central longitudinal axis of outer shaft 660, as shown. Inner shaft 610 extends through primary lumen 665 of the outer shaft. A first lumen 611, second lumen 615, third lumen 617 and fourth lumen 619 extend through inner shaft 610.

The fluid delivery balloon 620, first occlusion balloon 640 and second occlusion balloon 650 are fluidly operated by the various lumen extending through the in inner shaft 610 and outer shaft 660. Specifically, first lumen 611 connects in fluid communication with the second occlusion balloon 650, and is configured to inflate and deflate the second occlusion balloon with a gas or liquid. Secondary lumen 667 connects in fluid communication with first occlusion balloon 640, and is configured to inflate and deflate the second occlusion balloon with a gas or liquid. Second lumen 615 and third lumen 617 connect in fluid communication with the interior of fluid delivery balloon 620. Second lumen 615 is configured for filling fluid delivery balloon 620 with a MNP suspension, and third lumen 617 is configured for flushing out the fluid delivery balloon. The fourth lumen 619 receives and holds a guidewire 670 that is passed through the catheter.

Referring back to FIGS. 11 and 12, expandable mesh 630 is operable in two basic conditions: an expanded condition and a retracted condition. In the expanded condition, shown in FIG. 11, expandable mesh 630 extends radially outwardly from inner shaft 610, in relative proximity to a vessel wall V. In the retracted condition, shown in FIG. 12, expandable mesh 630 is positioned in relative proximity to inner shaft 610. This retracted condition keeps the outer extremity of expandable mesh 630 away from vessel wall V so that catheter 600 can be maneuvered more easily through the vessel.

The distal end 664 of the outer shaft 660 is connected with proximal end 632 of expandable mesh 630. Expansion and retraction expandable mesh 630 is controlled by adjusting the axial position of outer shaft 660 relative to inner shaft 610. Outer shaft 660 is axially displaceable relative to inner shaft 610 to a proximal position to move the expandable mesh to the retracted condition, and to a distal position to move the expandable mesh to the expanded condition. As such, outer shaft 660 can be "pushed" in a distal direction relative to inner shaft 610 to expand mesh 630, and "pulled" in a proximal direction relative to the inner shaft to retract the mesh.

Figure 15:
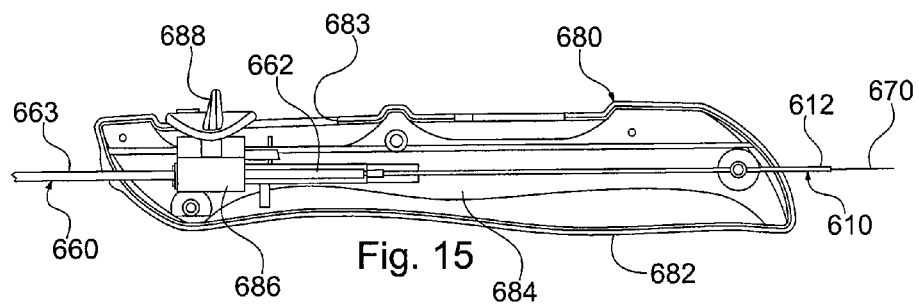
FIG. 15 is a magnified cross-sectional view of the magnetic targeting device in FIG. 10, partially truncated, showing features at the proximal end of the device in a first operative state.
Figure 16:
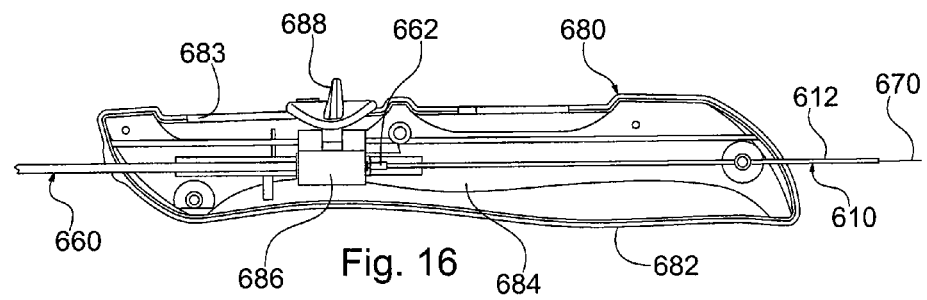
FIG. 16 is a magnified cross-sectional view of the magnetic targeting device in FIG. 10, partially truncated, showing features at the proximal end of the device in a second operative state.

Various mechanisms can be used to expand and retract the mesh. Referring to FIGS. 15 and 16, magnetic targeting catheter 600 features an integrated control handle 680. Control handle 680 includes a handle body 682 forming an inner chamber 684 that receives inner shaft 610, outer shaft 660 and guidewire 670. A slide member 686 is slidably displaceable in chamber 684 and fixed to the proximal end 662 of outer shaft 660. A thumb pad or button 688 is attached to slide member 686 through a slot 683 that extends through handle body 682. Outer shaft 660 is slidably displaceable over inner shaft in response to sliding movement of button 688 relative to handle body 682. Button 688 is moveable to a distal position, shown in FIG. 16, to push the outer shaft in the distal direction and place the mesh 630 in the expanded state. Button 688 is further moveable to a proximal position, shown in FIG. 17, to pull the outer shaft in the proximal direction and place the mesh 630 in a retracted state.

Magnetic Nanoparticles

MNP in accordance with the invention may include a magnetic field-responsive agent. As used herein, the term "magnetic field-responsive agent" means a paramagnetic, superparamagnetic, or ferromagnetic substance capable of moving under influence of a magnetic force. Superparamagnetic materials are preferred materials. In certain embodiments, the magnetic field-responsive agent is a member selected from the group consisting of iron, cobalt or nickel, alloys thereof, oxides thereof and mixed oxides/hydroxides of Fe(II) and/or Fe(III) with at least one of Co(II), Mn(II), Cu(II), Ni(II), Cr(III), Gd(III), Dy(III), and Sm(III). Preferably, the magnetic field-responsive agent is at least one of $Fe_3O_4$, gamma-$Fe_2O_3$, or a mixture thereof. Preferably, the magnetic field-responsive agent is iron oxide in a shape of nanocrystals. It may include magnetite/maghemite nanocrystals.

The magnetic field-responsive agent can be prepared by methods known in the art in various shapes and sizes. See Hyeon T., Chemical Synthesis of Magnetic Nanoparticles, The Royal Society of Chemistry 2003, Chem. Commun., 2003, 927-934, incorporated herein by reference. In certain embodiments, the agent may be iron oxide nanocrystals obtained by precipitation of mixed iron chlorides in the presence of a base in aqueous medium, as described by Khalafalla S E. Magnetic fluids, Chemtech 1975, September: 540-547, incorporated herein by reference. Because magnetic targeting involving superparamagnetic materials results in no permanent magnetic attraction after the magnetic field is discontinued, the system of the present invention preferably includes a surface modification of the MNP to enhance adhesion to the arterial wall after magnetic targeting.

Figure 17:
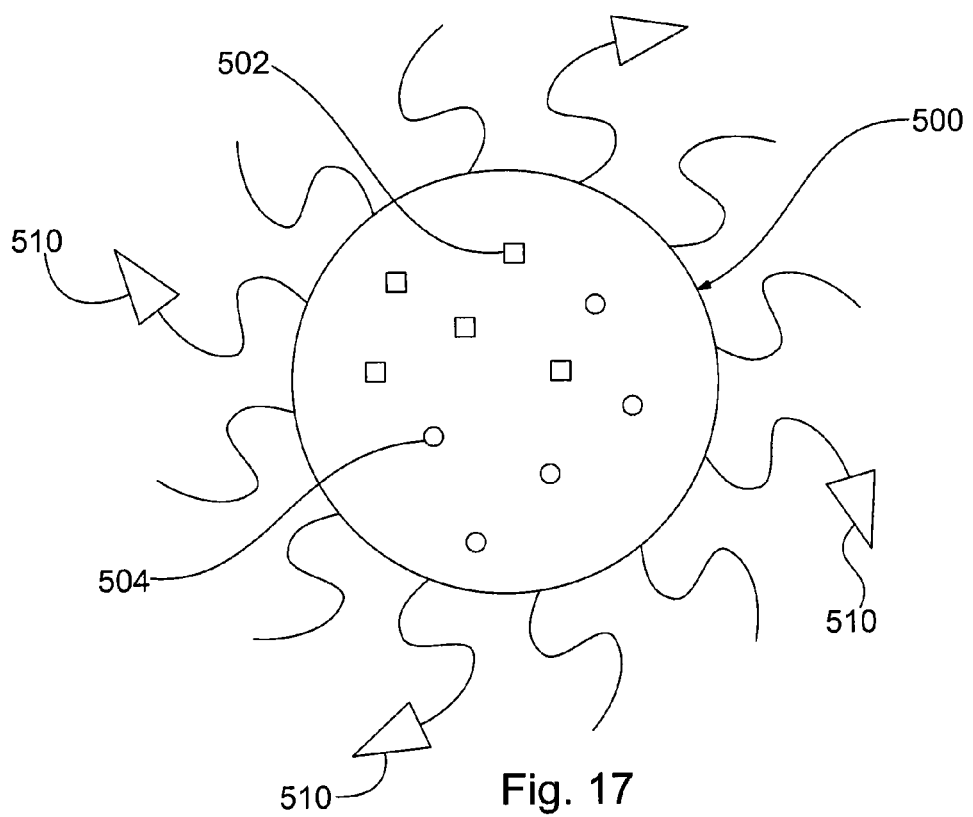
FIG. 17 illustrates one example of a magnetic nanoparticle suitable for use according to the invention.

FIG. 17 is an illustration of one type of magnetic nanoparticle 500 that can be used in accordance with the invention. Magnetic nanoparticle 500 contains iron oxide 502 and a therapeutic agent 504, such as an anti-restenotic drug (for example paclitaxel, a taxane, or sirolimus or an analog thereof) dispersed throughout the bulk for sustained release. Therapeutic agents other than these may also/instead be associated with MNP in accordance with the invention, including for example gene therapy vectors as described in U.S. patent publication number 2009/0082611, incorporated herein by reference. Or, recombinant proteins may be associated with the MNP, as described in Endothelial Delivery of Antioxidant Enzymes Loaded into Non-polymeric Magnetic Nanoparticles, Michael Chorny et al., Journal of Controlled Release 146 (2010) 144-151, incorporated herein by reference. MNP in accordance with the invention may also be associated with targeted cells preloaded therewith, as described for example in High Field Gradient Targeting of Magnetic Nanoparticle-loaded Endothelial Cells to the Surfaces of Steel Stents, Boris Polyak et al., Proc. Natl. Acad. Sci. 2008 Jan. 15; 105(2):698-703, incorporated herein by reference.

The MNP may be surface-modified with an appropriate ligand capable of binding to the surface of the angioplastied arterial wall to effect adhesion. In FIG. 17, magnetic nanoparticle 500 is surface-modified with ligands 510. Ligands in accordance with the invention may be one part of an antibody-antigen affinity pair, with the complementary part residing on the arterial wall. Alternatively, the ligands may be affinity peptides, or cell adhesion molecules such as cadherins, N-CAMs, selectins or immunoglobulins. Both types of ligands may be used in combination. Surface-modification of the nanoparticles with the ligands may be effected by any means known in the art, and the ligands may be attached to the nanoparticles via covalent binding and/or associative and/or ionic interactions with the nanoparticle. Examples of suitable surface modification methods are described in U.S. Pat. No. 7,635,734, incorporated herein by reference.

Surface-modifying the MNP, for example as described above, improves MNP retention in desired locations and reduces unintended delivery of the drug to distal organs, thereby maximizing therapeutic effects and minimizing possible undesired side effects.

Study—In Vivo Rat Carotid Stent Angioplasty with MNP Targeting

A study was performed with 500 gram rats (n=6 rats, 3 magnetic, mag+, and 3 nonmagnetic, mag−) under general anesthesia. The rats were subjected to left carotid stent angioplasty with a 304 stainless steel stent as described in Proc. Natl. Acad. Sci. USA. 2010 May 4; 107(18):8346-8351, the contents of which are incorporated herein by reference. A local infusion catheter was placed in the isolated carotid segment, and a dose of fluorescent magnetic nanoparticles comprising a 9:1 mixture of poly(D,L-lactide) and poly(D,L-lactide) covalently modified with BODIPY 564/570, nanocrystalline magnetite (30% by weight), and bovine serum albumin as a colloidal stabilizer was injected while a uniform magnetic field was applied (0.1 Tesla) across the stented region for five minutes. Each animal was then immediately euthanized, and the stented arterial segment was analyzed for arterial wall content of fluorescent MNP. The stent was removed for separate analyses for magnetic nanoparticle levels, and those levels were compared to levels observed at the stented arterial wall segment. Control animals were subjected to the same stent and MNP administration, but without exposure to a magnetic field.

FIG. 1 shows levels of magnetic nanoparticle retention on a superparamagnetic stent and on an arterial wall (rat carotid) in the presence and in the absence of a uniform magnetic field (0.1 T) that was applied for 5 minutes. Fluorescence assays were used to calculate the uptake values (FIG. 1, mean+/−s.d.). The results indicate that after only five minutes there was more than four-fold greater arterial wall uptake by the stented artery with magnetic field exposure than with controls without magnetic field exposure. For the sample exposed to the magnetic field, roughly 60% of the MNP retained after 5 minutes was associated with the stent (probably due to adherent tissue, thrombus, proteins) and 40% was associated with the arterial wall. The 304 stents, being superparamagnetic, did not become permanently magnetized following magnetic field exposure and thus had no magnetic remanence after discontinuation of the field. Thus, these in vivo data demonstrate magnetic targeting using a temporary stent and only a brief magnetic field exposure, obviating the need to leave the stent in place after treatment. Accordingly, the data indicates that comparable results can be achieved with a temporarily placed device, such as a magnetic targeting catheter in accordance with the invention.

The devices, systems and methods of this invention provide significant advantages over using permanently implanted, superparamagnetic steel stents as targets for magnetic nanoparticles. Magnetic targeting catheters in accordance with the invention can be used in virtually any site permitting catheter access. In addition, magnetic targeting catheters enable MNP delivery to a site where one or more stents may already be present. The invention also enables the physician to pretreat a desired area with MNP prior to implanting a permanent stent. This provides the ability to perform multiple interventions along the length of an arterial segment, regardless of the presence or absence of stents.

The systems and methods of this invention may also be used in situations where permanent stent placement is undesirable. For example, current recommendations by TASC II (the TransAtlantic Inter-Society Consensus group for treating PAD) recommends that TASC A lesions, defined as 3 cm or less in length and not at the origin of the superficial femoral artery, that are causing critical limb ischemia, be treated exclusively with balloon angioplasty, in view of equivalent outcomes for this versus permanent stent placement. In one aspect of the invention, such sites may be targeted with MNP either before or after balloon angioplasty, or instead of balloon angioplasty, using only a magnetic targeting catheter positioned in a uniform magnetic field.

In some embodiments of the invention, the magnetic targeting catheter is passed through a previously placed permanent stent and then deployed and targeted with MNP at a site beyond the location of the permanent stent. Similarly, a magnetic targeting catheter may be deployed and targeted inside an already-deployed permanent stent, for example in cases where in-stent restenosis has occurred. These capabilities provide flexible treatment options permitting reinterventions at virtually any desired location and any desired time interval. As outlined above, the skilled artisan will recognize that many of the options available with magnetic targeting catheters would be not be available if a permanent stent were used.

As noted above, magnetic targeting catheters in accordance with the invention may be made using a custom made catheter. In such a design, the catheter portion may utilize a variety of fluid connections and controls. For example, the catheter may include a standard connection for connecting the inflation tube to a source of fluid. Likewise, the catheter portion may utilize a standard connection for connecting the injection tube to a source of MNP or cells loaded with MNP. Alternatively, the injection tube can be preloaded with MNP or cells loaded with MNP prior to inserting the magnetic targeting catheter into the patient. Where the device includes a control rod, the control rod may be connected to a separate device for gripping and moving the control rod, or a control assembly that is built into the proximal end of the catheter. Each control rod may be movable manually, with the assistance of a battery powered gear assembly, or other means.

Figure 10:
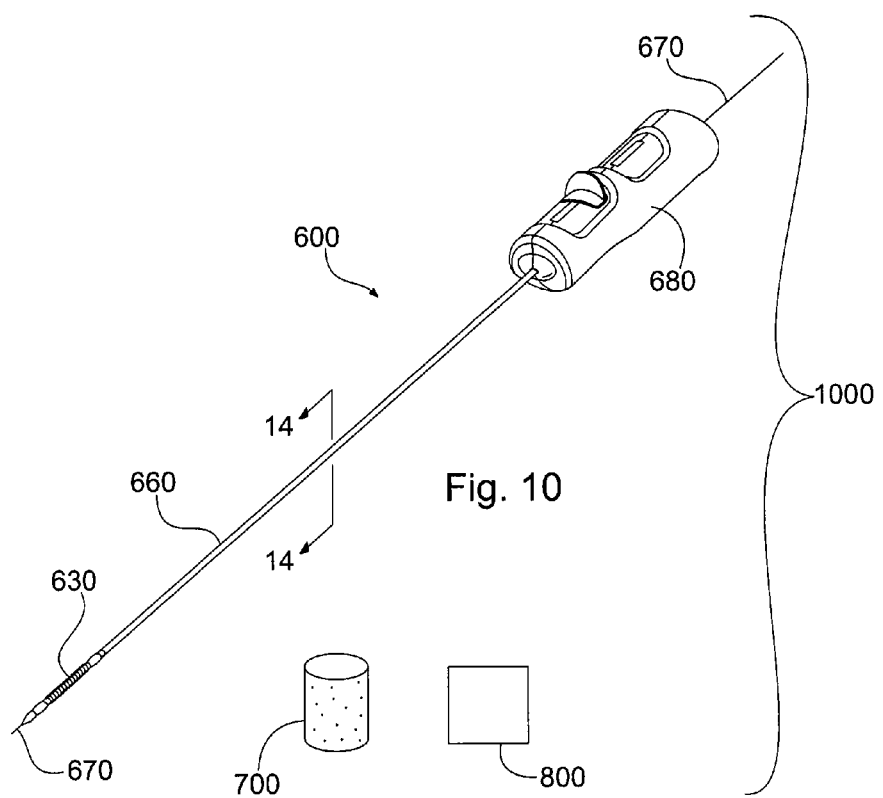
FIG. 10 is a perspective view of a kit in accordance with the invention showing another magnetic targeting device in accordance with the invention.
Figure 11:
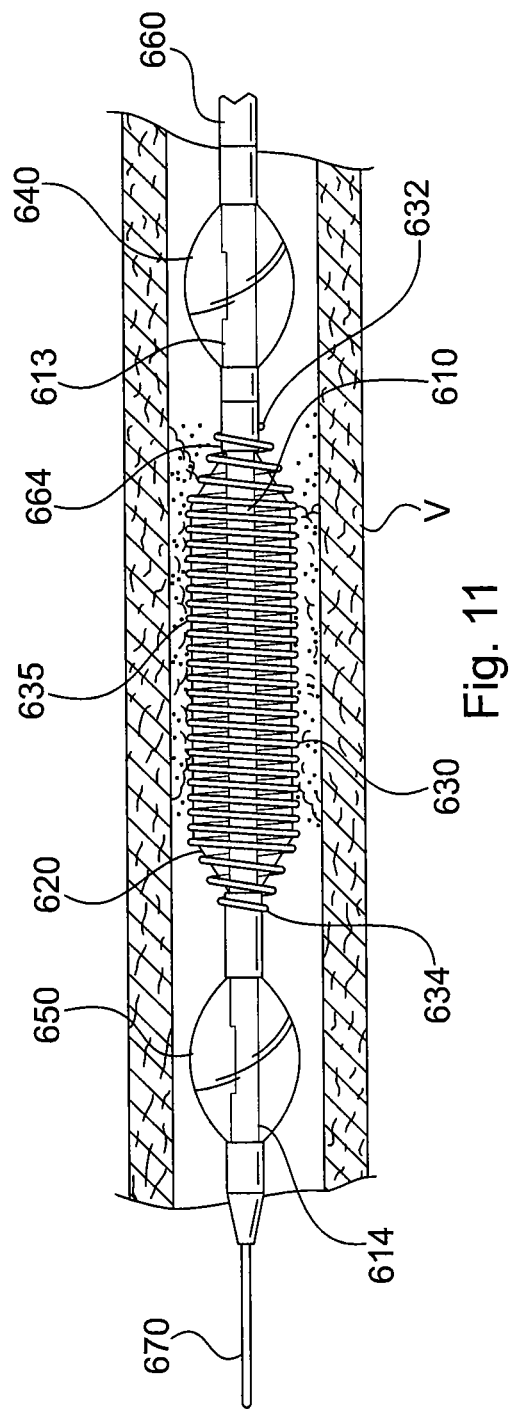
FIG. 11 is a magnified perspective view of the magnetic targeting device in FIG. 10, partially truncated, showing features at the distal end of the device in a first operative state.
Figure 12:
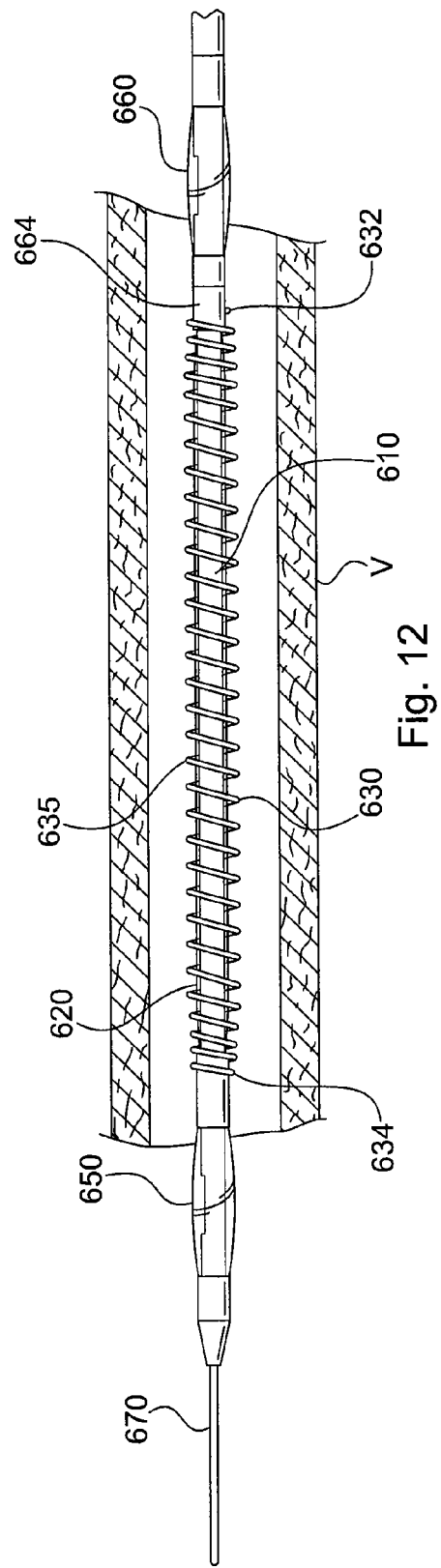
FIG. 12 is another magnified perspective view of the magnetic targeting device in FIG. 10, partially truncated, showing features at the distal end of the device in a second operative state.
Figure 13:
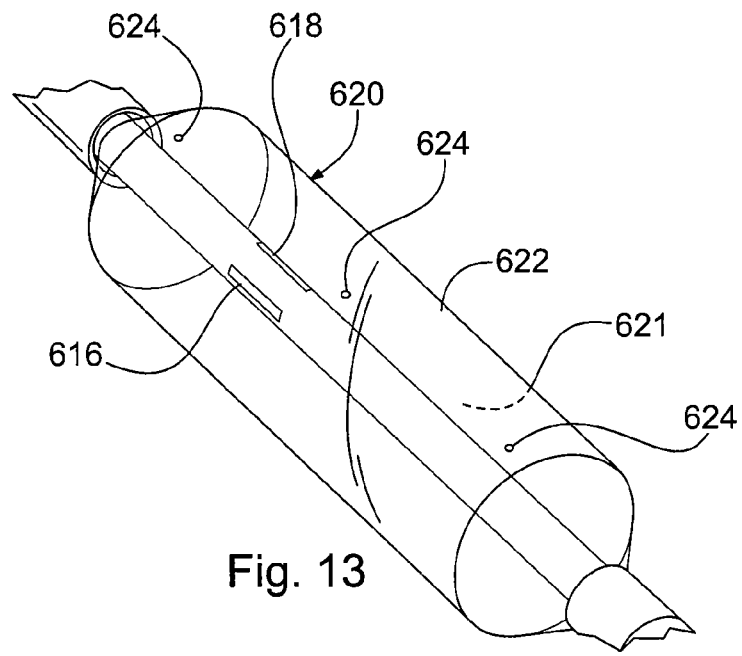
FIG. 13 is a magnified perspective view of components of the magnetic targeting device in FIG. 10, partially truncated with a component removed, showing additional features at the distal end of the device.

Systems in accordance with the invention may be packaged and sold or otherwise distributed in the form of a kit. FIG. 10, for example, shows a kit 1000 that includes the magnetic targeting catheter 600, a MNP suspension 700 to be administered through the magnetic targeting catheter, and a source for generating a uniform magnetic field 800, such as permanent magnets or electromagnets.

Although the invention is illustrated and described herein with reference to specific embodiments, the invention is not intended to be limited to the details shown. Rather, various modifications may be made in the details within the scope and range of equivalents of the claims without departing from the invention. In addition, features shown and described in some embodiments, and/or features recited in some claims, may be combined and/or interchanged with features of other embodiments that are described or claimed without departing from the invention.

What is claimed is:

1. A system for treating a medical condition in a human or animal, the system comprising:
    a) a magnetic targeting catheter comprising as an integral component a mesh or snare comprising a temporarily magnetizable material; and
    b) magnetic nanoparticles comprising one or more magnetic field-responsive agents and one or more therapeutic agents;
wherein the mesh or snare is expandable and subsequently collapsible while inserted in the human or animal during the treatment, and is configured to remain integral with the catheter during the entirety of the treatment.

2. The system of claim 1, wherein the nanoparticles have on a surface thereof ligands capable of enhancing adhesion to a targeted site in the human or animal.

3. The system of claim 1, wherein the magnetic targeting catheter is surface-modified with moieties that promote reversible adhesion of the MNP thereto.

4. The system of claim 1, wherein the temporarily magnetizable material comprises a material from the group consisting of stainless steel and nickel-iron-molybdenum alloy.

5. The system of claim 1, wherein the one or more magnetic field-responsive agents comprise a temporarily magnetizable material.

6. The system of claim 1, wherein the one or more magnetic field-responsive agents include iron oxide.

7. The system of claim 1, wherein the one or more therapeutic agents comprise taxol or a taxane.

8. The system of claim 1, wherein the one or more therapeutic agents comprise sirolimus or an analogue thereof.

9. The system of claim 1, wherein the one or more therapeutic agents comprise gene therapy vectors and/or recombinant proteins, and/or wherein the magnetic nanoparticles are included in targeted cells preloaded therewith.

10. The system of claim 1, further comprising a magnetic or magnetizable arterial filter.

11. The system of claim 10, wherein the magnetic or magnetizable arterial filter is deployable at a location downstream of the distal end of the magnetic targeting catheter.

12. The system of claim 1, further comprising an occlusion balloon.

13. The system of claim 12, wherein the magnetic targeting catheter comprises the occlusion balloon as an integral component.

14. A method of treating a medical condition in a human or animal with one or more therapeutic agents, comprising the steps of
    a) advancing a magnetic targeting catheter to a site in the human or animal in need of the one or more therapeutic agents;
    b) deploying an expandable mesh or snare connected at the distal end of the magnetic targeting catheter, the mesh or snare comprising a temporarily magnetizable material;
    c) applying a uniform magnetic field to the mesh or snare sufficient to temporarily magnetize the mesh or snare;
    d) while applying the magnetic field of step c), depositing near the mesh or snare a plurality of MNP comprising one or more magnetic field-responsive agents and the one or more therapeutic agents, wherein the nanoparticles have on a surface thereof ligands capable of enhancing adhesion to tissue at the site;
    e) undeploying the mesh or snare; and
    f) moving the magnetic targeting catheter to another location in the human or animal;

wherein the expandable mesh or snare remains connected to the distal end of the magnetic targeting catheter while the method is being performed.

15. The method of claim 14, further comprising after step e) but before step f) at least one repetition of steps a) through e) at one or more additional sites in need of treatment.

16. The method of claim 14, further comprising a step of deploying a magnetic or magnetizable arterial filter downstream of a site in need of treatment prior to depositing the plurality of MNP.

17. The method of claim 14, further comprising after step f) a step g) that comprises implanting a permanent stent at a site that has been treated according to steps a) through f).

18. The method of claim 14, wherein step a) includes passing the mesh or snare through a previously placed permanent stent.

19. The method of claim 14, wherein the deploying step of step b) is performed inside an already-deployed permanent stent.

20. The method of claim 14, wherein the site is in an artery.

21. A device for treating a medical condition in a human or animal, the device comprising:
   a catheter comprising a hollow tubular body; and
   a delivery assembly attached to a distal end of the catheter, the delivery assembly comprising:
      an inflation tube extending through the catheter, the inflation tube having a distal end;
      an inner balloon attached to the distal end of the inflation tube;
      an injection tube extending through the catheter, the injection tube having a distal end;
      an outer balloon attached to the distal end of the injection tube and enclosing the inner balloon, the outer balloon comprising a wall that is perforated by a plurality of pores extending through the wall;
      a control rod extending through the catheter, the control rod having a distal end; and
      a mesh attached to the distal end of the control rod and surrounding at least a portion of the outer balloon.

22. The device of claim 21, further comprising a source of gas or liquid fluidly connected to the inflation tube.

23. The device of claim 21, further comprising a suspension of MNP or cells loaded with MNP.

24. The device of claim 23, wherein the suspension of MNP or cells loaded with MNP are contained in a source that is fluidly connected to the injection tube.

25. The device of claim 23, wherein the suspension of MNP or cells loaded with MNP are contained in the injection tube.

26. The device of claim 21, wherein the mesh is formed of a temporarily magnetizable material.

27. The device of claim 26, wherein the temporarily magnetizable material is selected from the group consisting of 304 stainless steel and a nickel-iron-molybdenum alloy.

28. A method of treating a medical condition in a human or animal with one or more therapeutic agents, comprising the steps of
   a) advancing a magnetic targeting catheter to a site in the human or animal in need of the one or more therapeutic agents;
   b) deploying an expandable mesh or snare connected at the distal end of the magnetic targeting catheter, the mesh comprising a temporarily magnetizable material;
   c) applying a magnetic field to the mesh or snare sufficient to temporarily magnetize the mesh;
   d) while applying the magnetic field of step c), depositing near the mesh or snare a plurality of cells loaded with MNP comprising one or more magnetic field-responsive agents and the one or more therapeutic agents;
   e) undeploying the mesh or snare; and
   f) moving the magnetic targeting catheter to another location in the human or animal;
wherein the expandable mesh or snare remains connected to the distal end of the magnetic targeting catheter while the method is being performed.

29. A catheter device for delivering a fluid into a vessel, the catheter device comprising:
   an inner shaft comprising a proximal end, a distal end, and a hollow body extending between the proximal end and distal end, the hollow body forming at least one lumen extending through the inner shaft from the proximal end to the distal end;
   a fluid delivery balloon adapted to administer a fluid from the inner shaft into a vessel surrounding the catheter, the fluid delivery balloon comprising a balloon wall surrounding an interior space, the balloon wall forming at least one opening that extends through the balloon wall, the balloon wall disposed around a distal portion of the inner shaft, with the distal portion of the inner shaft comprising at least one port in fluid communication with the interior space of the fluid delivery balloon; and
   an expandable mesh surrounding the fluid delivery balloon, the expandable mesh having a proximal end and a distal end, and formed of a magnetizable material.

30. The catheter device of claim 29, further comprising at least one occlusion balloon adapted to inflate and constrict a section of a vessel surrounding the catheter device.

31. The catheter device of claim 30, wherein the at least one occlusion balloon comprises a first occlusion balloon located proximally with respect to the expandable mesh and a second occlusion balloon located distally with respect to the expandable mesh.

32. The catheter device of claim 31, further comprising an outer shaft extending over at least a portion of the inner shaft, the outer shaft comprising a proximal end, a distal end, and hollow body extending between the proximal end and distal end of the outer shaft.

33. The catheter device of claim 32, wherein the hollow body of the outer shaft forms a primary lumen and a secondary lumen, the primary and secondary lumens extending from the proximal end of the outer shaft to the distal end of the outer shaft.

34. The catheter device of claim 33, wherein the inner shaft extends through the primary lumen of the outer shaft.

35. The catheter device of claim 33, wherein the secondary lumen of the inner shaft connects in fluid communication with the first occlusion balloon.

36. The catheter device of claim 33, wherein the at least one lumen of the inner shaft comprises a first lumen in fluid communication with the second occlusion balloon.

37. The catheter device of claim 36, wherein the at least one lumen comprises a second lumen in fluid communication with the interior of the fluid delivery balloon.

38. The catheter device of claim 37, wherein the at least one lumen comprises a third lumen in fluid communication with the interior of the fluid delivery balloon.

39. The catheter device of claim 38, wherein the at least one lumen comprises a fourth lumen adapted to receive a guidewire through the catheter device.

40. The catheter device of claim 39 further comprising a guidewire extending through the fourth lumen.

41. The catheter device of claim 32, wherein the distal end of the outer shaft is connected with the proximal end of the expandable mesh.

42. The catheter device of claim 41, wherein the expandable mesh is operable in a retracted condition, in which the expandable mesh is positioned in relative proximity to the inner shaft for maneuvering the catheter device through a vessel, and an expanded condition, in which the expandable mesh extends radially outwardly from the inner shaft for positioning in relative proximity to a vessel wall.

43. The catheter device of claim 42, wherein the outer shaft is axially displaceable relative to the inner shaft to a proximal position to move the expandable mesh to the retracted condition, and a distal position to move the expandable mesh to the expanded condition.

44. The catheter device of claim 43, further comprising a control handle and a control button connected to the outer shaft, the control button slidably displaceable relative to the control handle to a first position to move the outer shaft to the proximal position and place the expandable mesh in the retracted condition, and the control button slidably displaceable relative to the control handle to a second position to move the outer shaft to the distal position and place the expandable mesh in the expanded condition.

45. The method of claim 14, wherein the step of applying a uniform magnetic field comprises the step of using a dipole or more complex magnetic array.

46. The method of claim 14, further comprising the step of ceasing application of the uniform magnetic field to the mesh or snare, wherein the MNP are released into the site upon cessation of the uniform magnetic field.

* * * * *